United States Patent
Sears

(10) Patent No.: US 9,615,956 B2
(45) Date of Patent: Apr. 11, 2017

(54) ORTHOPEDIC CLAVICLE BRACE

(76) Inventor: Jack T. Sears, Spearfish, SD (US)

( * ) Notice: Subject to any disclaimer, the term of this patent is extended or adjusted under 35 U.S.C. 154(b) by 732 days.

(21) Appl. No.: 13/565,048

(22) Filed: Aug. 2, 2012

(65) Prior Publication Data

US 2014/0039370 A1    Feb. 6, 2014

(51) Int. Cl.
*A61F 5/058*    (2006.01)
*A61F 5/02*    (2006.01)

(52) U.S. Cl.
CPC .......... *A61F 5/026* (2013.01); *A61F 5/05808* (2013.01)

(58) Field of Classification Search
CPC ..................................................... A61F 5/0118
USPC ..................................... 602/19, 20, 5, 1, 6–8
See application file for complete search history.

(56) References Cited

U.S. PATENT DOCUMENTS

| | | | |
|---|---|---|---|
| 139,366 A * | 5/1873 | Burnap | ................................ 2/44 |
| 198,503 A | 12/1877 | Altmann | |
| 531,372 A | 12/1894 | Gamble | |
| 877,560 A * | 1/1908 | Foltz | .................................. 2/44 |
| 2,450,298 A | 9/1948 | Peterson et al. | |
| 3,499,441 A | 3/1970 | Hall | |
| 3,548,818 A | 12/1970 | Kaplan | |
| 3,856,004 A | 12/1974 | Cox | |
| 3,857,388 A * | 12/1974 | Frankel | ........................... 602/19 |
| 4,570,619 A | 2/1986 | Gamm | |
| 4,589,406 A | 5/1986 | Florek | |
| 5,120,288 A * | 6/1992 | Sinaki | ........................... 482/105 |
| 5,133,340 A | 7/1992 | Koopmann | |
| 6,315,747 B1 | 11/2001 | Toole | |
| 6,936,021 B1 | 8/2005 | Smith | |
| 6,991,611 B2 | 1/2006 | Rhee | |
| 8,308,670 B2 * | 11/2012 | Sandifer et al. | ................. 602/19 |
| 8,556,840 B2 * | 10/2013 | Burke et al. | ..................... 602/19 |
| 2004/0147861 A1 * | 7/2004 | Kozersky | ......................... 602/19 |
| 2006/0129076 A1 * | 6/2006 | Haneda | ........................... 602/19 |
| 2010/0318010 A1 * | 12/2010 | Sandifer et al. | ................. 602/19 |

* cited by examiner

*Primary Examiner* — Tarla Patel
(74) *Attorney, Agent, or Firm* — McKee, Voorhees & Sease, PLC

(57) ABSTRACT

An easily-accessible, self-adjustable orthopedic clavicle brace and method of use for preventing and treating damage to the clavicle. The brace supports the shoulder region of a user's body during the healing or mending of an injured, dislocated, fractured or broken clavicle. The device uses a simple coupling means located towards the front of the user to allow for easy accessibility by the user for self-application, self-adjustment, and self-removal of the brace without having to rely on assistance by a second party.

17 Claims, 4 Drawing Sheets

ORTHOPEDIC CLAVICLE BRACE

FIELD OF THE INVENTION

The present invention relates to an easily-accessible, self-adjustable orthopedic clavicle brace and method of use for preventing and treating damage to the clavicle. Such a device would support the shoulder region of a user's body during the healing or mending of an injured, dislocated, fractured or broken clavicle. The purpose of the device is to stretch the clavicle longitudinally and immobilize it such that the surfaces of the fracture will fit and grow together rather than grind against one another. The device uses a simple coupling means located towards the front of the user to allow for easy accessibility by the user for self-application, self-adjustment, and self-removal of the brace without having to rely on assistance by a second party.

BACKGROUND OF THE INVENTION

The function of the clavicle bones in the human body is to serve as a strut between the scapula and the sternum. Clavicle bones are joined by one end to the sternum and are joined at the opposite end to the scapula. Clavicle bones are frequently fractured as being the only connection between the shoulders and the trunk of the body. Displacement of clavicle bone fractures is reduced by pulling the shoulders horizontally, longitudinally and rearward while maintaining this position. Suitable orthopedic braces for applying horizontal, longitudinal and rearward forces to the shoulders allow fractured fragments to unite and heal by removing pressure and eliminating excess motion.

Shoulder or clavicle orthopedic braces are well known in the art. One type of shoulder or clavicle brace well known in the art is of a generally figure-8 shaped configuration. In this figure-8 type shoulder brace, the crossover location of the brace's right and left shoulder loops overlies the user's back, the user's arms extending through the shoulder loops when the brace is being worn. This type of brace typically includes a pad combined with each strap which overlies the user's shoulders, the pad extending under the user's axilla, or armpit, so as to tend to minimize biting or discomfort of the straps against the user's torso when the brace is being worn. In figure-8 type shoulder braces, it is important that the shoulder straps be provided with an adjustable fastener by which the loops can be increased or decreased in size. This allows for the brace to be sized initially depending on the upper body size of the user, and also allows for the shoulder loops to be tightened or loosened after the brace has been installed on the user as required or desired by the user and/or attending physician. Typically, each such adjustable fastener is in the form of a buckle that cooperates with the free end of its associated shoulder strap, the buckle being connected to the brace in the center of the user's back when the brace is being worn. Other adjustable fasteners may also be utilized, such as VELCRO® hook and loop fasteners, D-rings, or strap clips as utilized on back-packs. Most fasteners by which a figure-8 type shoulder brace's shoulder straps are adjustably lengthened or shortened involve some kind of fastener device that, after the brace is installed on the user, is located in or closely adjacent to the center of the user's back.

The location of adjustable fasteners in the middle of a user's back when a figure-8 type shoulder brace is being worn results in a significant practical disadvantage to the user. This location of the adjustable fasteners requires that a second person must stand behind the user to initially adjust the shoulder strap length to a desired beginning length if such is to be achieved when the brace is in place, and also requires that a second person stand in back of the user to subsequently adjust the tightness or looseness of the shoulder straps as the brace is worn during everyday life by the user. In other words, the user himself/herself cannot initially set the length of the shoulder straps in a final desired or required position while wearing the prior art figure-8 type shoulder braces, and the user himself/herself cannot adjust the tightness or looseness of the shoulder straps on that type brace as the brace becomes tighter or looser while being worn during everyday life. Obviously this is a disadvantage of substantial significance to users of prior art shoulder braces when no second person is around to help with desired shoulder strap adjustments. In other words, these types of figure-8 type braces cannot be adjusted by the user while the shoulder brace is being worn.

BRIEF SUMMARY OF THE INVENTION

The present invention is directed towards overcoming the problems and disadvantages in previous figure-8 clavicle braces. An object of the present invention is to provide an orthopedic clavicle brace that pulls at the correct angle to the injured clavicle to promote healing and support while allowing easy accessibility to the user for making self-adjustments without having to rely on assistance by a second party. It is still a further object of the invention to provide a clavicle brace which may be easily adjusted for various sizes and shapes of persons and which may be easily applied and removed.

A preferred embodiment of the present invention discloses a universal clavicle brace for positioning over the upper back of the user including a triangular shaped clavicle brace support body comprising three adjustable fasteners at each corner of the body. A T-shaped shoulder strap with three ends is coupled to an adjustable fastener on the top corner portion of the body by a first end of the shoulder strap. A second end of the shoulder strap extends over a first shoulder of the user. A third end of the shoulder strap extends over a second shoulder of the user. Each second and third end of the shoulder strap includes an adjustable fastener secured thereon opposite the first end attached to the body. A first axilla strap is coupled to an adjustable fastener on the bottom corner portion of the body by one end of the axilla strap. The first axilla strap has a distal end for extending under one axilla of the user, and is coupled to the adjustable fastener secured to the second end of the shoulder strap. A second axilla strap is coupled to an adjustable fastener on the opposite lower corner portion of the body adjacent the first axilla strap. The second axilla strap has a distal end for extending under the second axilla of the user, and is coupled to the adjustable fastener secured to the third end of the shoulder strap. The adjustable fasteners allow for adjustment and tightening of the straps, in addition to application and removal of the brace. The location of the adjustable fasteners towards the front of the user allows for easy accessibility by the user for making self-adjustments, self-application and self-removal of the brace without having to rely on assistance by a second party.

A preferred method of the present invention for giving support to a user's shoulders to prevent or treat damage to an injured clavicle provides: a clavicle brace support body; a shoulder strap attached to said clavicle brace support body, the shoulder strap extending over a first shoulder and a second shoulder of a user; a first axilla strap attached to said clavicle brace support body, the axilla strap extending under a first axilla of the user; a second axilla strap attached to the clavicle brace support body, the second axilla strap extending under a second axilla of the user; attaching the shoulder strap to the first axilla strap at a first location towards a front of the user; attaching the shoulder strap to the second axilla strap at a second location towards a front of the user; and, self-applying, self-adjusting or self-removing the clavicle brace support body by the user without needing a second party for assistance. Typically, the means of attachment include adjustable fasteners such as buckles. Additional adjustable fasteners may also be utilized, such as VELCRO® hook and loop fasteners, D-rings, or strap clips as utilized on back-packs.

Different embodiments may meet different objects of the invention. Other objectives and advantages of this invention will be more apparent in the following detailed description taken in conjunction with the figures. The present invention is not to be limited by or to these objects.

DESCRIPTION OF FIGURES

FIG. 1 is a rear view of a user wearing the orthopedic clavicle brace of the present invention utilizing a T-shaped shoulder strap and two separate axilla straps.

FIG. 2 is a front view of a user wearing the orthopedic clavicle brace of the present invention.

FIG. 3 is a rear view of a user wearing another embodiment of an orthopedic clavicle brace of the present invention utilizing two separate shoulder straps and a T-shaped axilla strap.

FIG. 4 is a view of a portion of the present invention showing how the adjustable fastener provides a coupling means for attaching shoulder straps to axilla straps, and for attaching shoulder and axilla straps to the clavicle brace support body.

FIG. 5 is a section view of a portion of the present invention showing how another embodiment of an adjustable fastener provides a coupling means for attaching shoulder straps to axilla straps, and for attaching shoulder and axilla straps to the clavicle brace support body.

FIG. 6 is a rear view of a user wearing an embodiment of an orthopedic clavicle brace of the present invention wherein the clavicle brace support body is formed integrally with the axilla straps and the shoulder strap is attached to the body by a D-ring.

FIG. 7 is a rear view of a user wearing another embodiment of an orthopedic clavicle brace of the present invention utilizing two separate shoulder straps and two separate axilla straps.

DETAILED DESCRIPTION OF THE INVENTION

Figure 1:
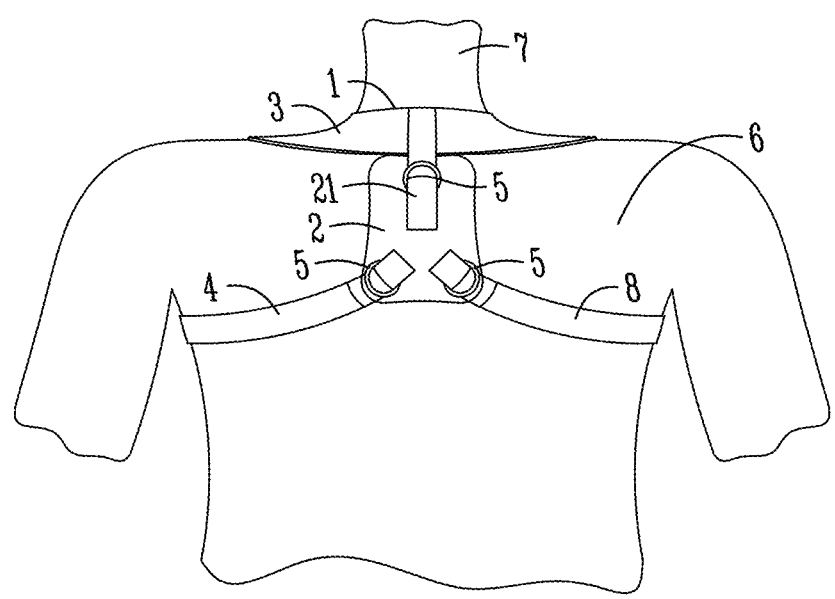
FIGS. 1-7 represent examples of orthopedic clavicle braces of the present invention.
Figure 2:
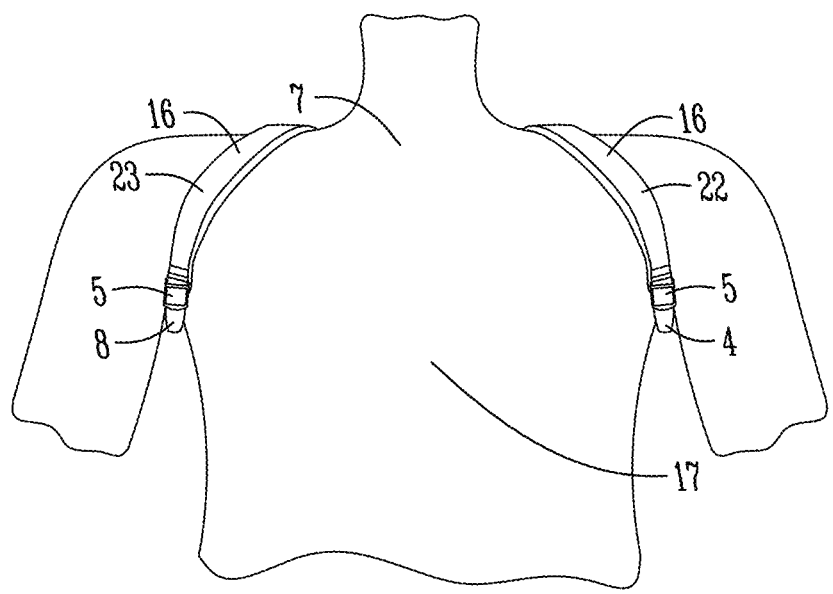

The orthopedic clavicle brace (1) of the present invention and method for use is for giving support to a user's shoulders to prevent injury and to promote healing of a dislocated, injured or fractured clavicle. A preferred embodiment of the brace (1) includes: a clavicle brace support body (2); a shoulder strap (3); a first axilla strap (4); a second axilla strap (8); and, adjustable fasteners (5). See FIG. 1. The clavicle brace support body (2) is configured to position substantially over the upper back (6) of the user (7). The shoulder strap (3), T-shaped and having three end portions (21, 22, 23), is attached to the upper portion of the body (2) by a proximal first end portion (21) of the strap (3). Portions of the shoulder strap (3) extending around the neck and over the shoulders of the user (7) are typically wider than the first end portion (21) of the shoulder strap (3) coupled to the body (2). This extra width provides additional support to the injured clavicle and neck of the user (7). A second end portion (22) of the shoulder strap (3) is for extending over a first shoulder of the user (7). A third end portion (23) of the shoulder strap (3) is for extending over a second shoulder of the user (7). The first axilla strap (4) is attached to the lower portion of the body (2) and has a distal end portion for extending under a first axilla of the user (7). The second axilla strap (8) is attached to the lower portion of the body (2) adjacent to the first axilla strap (4) and has a distal end portion for extending under a second axilla of the user (7). The second end portion (22) of the shoulder strap (3) extending over the first shoulder of the user (7) includes an adjustable fastener (5) thereon for allowing the second end portion (22) of the shoulder strap (3) to be attached to the distal end portion of the first axilla strap (4) extending under the first axilla of the user (7). Likewise, the third end portion (23) of the shoulder strap (4) extending over the second shoulder of the user (7) includes an adjustable fastener (5) thereon for allowing the third end portion (23) of the shoulder strap (3) to be attached to the distal end portion of the second axilla strap (8) extending under the second axilla of the user (7). Notably, the location of the adjustable fastener (5) for attaching the second end portion (22) of the shoulder strap (3) to the first axilla strap (4), and the location of the adjustable fastener (5) for attaching the third end portion (23) of the shoulder strap (3) to the second axilla strap (8) is towards the front (17) of the user (7). These locations allow the user (7) to personally apply the brace (1), remove the brace (1), tighten the straps (3, 4, 8) or adjust the brace (1) without the assistance of a second person. In the preferred embodiment, the clavicle brace support body (2) is triangular in shape, although it is recognized that other shapes may be utilized. The triangular shape insures that there are equal and opposing forces from the shoulder strap (3) and axilla straps (4, 8).

Figure 3:
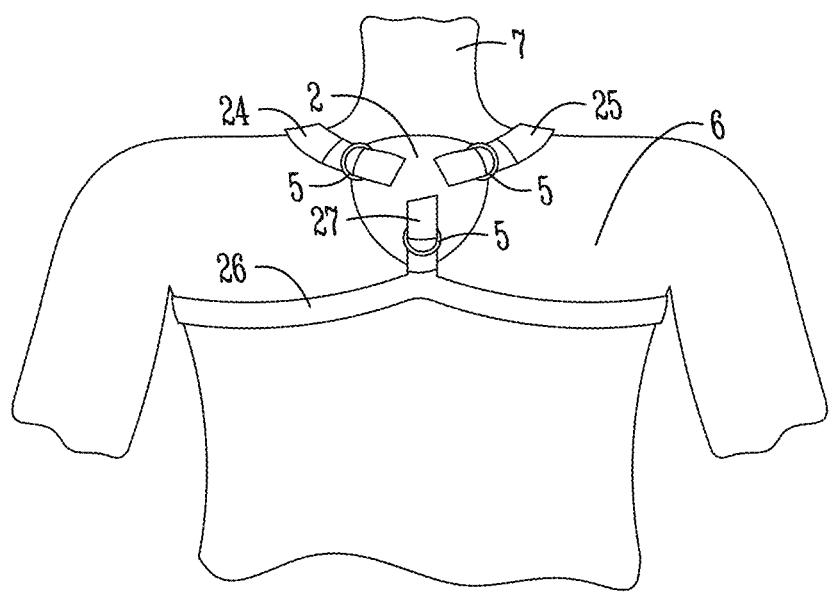
Figure 7:
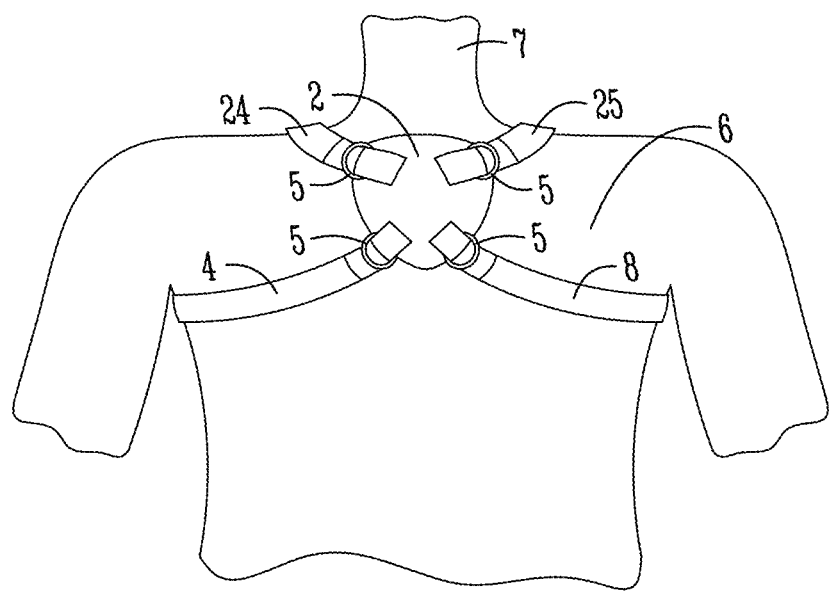

Another embodiment of the orthopedic clavicle brace (1) of the present invention includes a clavicle brace support body (2), a first shoulder strap (24), a second shoulder strap (25), and adjustable fasteners (5). See FIG. 3. The clavicle brace support body (2) is configured to position substantially over the upper back (6) of the user (7). The first shoulder strap (24) is attached to the upper portion of the body (2) and has a distal end portion for extending over a first shoulder of the user (7). The second shoulder strap (25) is attached to the upper portion of the body (2) adjacent the first strap (24) and has a distal end portion for extending over a second shoulder of the user (7). An axilla strap (26), T-shaped and having three ends, is attached to the lower portion of the body (2) by a proximal first end portion (27) of the strap (26). The second end portion of the axilla strap (26) is for extending under one axilla of the user (7). The third end portion of the axilla strap (26) is for extending under the second axilla of the user (7). The distal end portion of the first shoulder strap (24) extending over the first shoulder of the user (7) includes an adjustable fastener (5) thereon for allowing the distal end portion of the first shoulder strap (24) to be attached to the second end portion of the axilla strap (26) extending under the first axilla of the user (7). Likewise, the distal end portion of the second shoulder strap (25) extending over the second shoulder of the user (7) includes an adjustable fastener (5) thereon for allowing the distal end portion of the second shoulder strap (25) to be attached to the third end portion of the axilla strap (26) extending under the second axilla of the user (7). Similar to the preferred embodiment, the location of the adjustable fastener (5) for attaching the first shoulder strap (24) to the axilla strap (26) and the location of the adjustable fastener (5) for attaching the second shoulder strap (25) to the axilla strap (26) is towards the front (17) of the user (7). These locations allow the user (7) to personally apply the brace (1), remove the brace (1), tighten the straps (24, 25, 26) or adjust the brace without the assistance of a second person. A further embodiment of the present invention may utilize two shoulder straps (24, 25) in place of the previously mentioned (T-shaped) shoulder strap (3) and two axilla straps (4, 8) in place of the previously mentioned (T-shaped) axilla strap (26). See FIG. 7.

Figure 4:
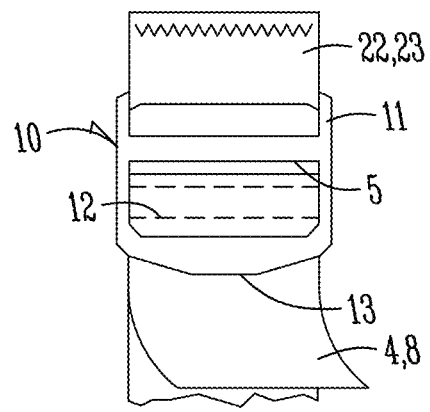

The preferred embodiment of the invention includes a buckle (10) as the adjustable fastener (5). See FIG. 4. The buckle (10) may be constructed of a plastic or metal material. The second end portion (22) of the shoulder strap (3) is substantially fixedly coupled to a buckle (10) through a fabric loop (11). The third end portion (23) of the shoulder strap (3) is also substantially fixedly coupled to another buckle (10) through a fabric loop (11). An end portion (22, 23) of the shoulder strap (3) is wrapped around the fabric loop (11) and then substantially fixedly coupled upon itself through stitching, an adhesive, or both. A distal end portion of an axilla strap (4, 8) is coupled to a buckle (10) coupled to an end portion (22, 23) of the shoulder strap (3) through a second fabric loop (12). A distal end portion of an axilla strap (4, 8) is wrapped around the second fabric loop (12) and folded under the placement tab (13). This allows for a user to pull on a distal end portion of an axilla strap (4, 8) to apply the brace, and tighten or adjust the brace accordingly. This will also allow a user (7) to remove the orthopedic clavicle brace by loosening a distal end portion of an axilla strap (4, 8) from around the second fabric loop (12).

Figure 5:
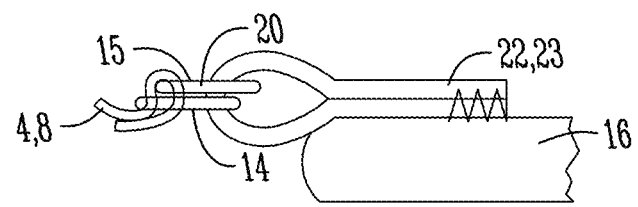

A second embodiment of a buckle (20) is depicted in FIG. 5. In the buckle (20) of FIG. 5, an end portion (22, 23) of the shoulder strap (3) is substantially fixedly coupled to two rings (14, 15). The end portion (22, 23) is looped through both rings (14, 15) and then substantially fixedly coupled upon itself through stitching, an adhesive, or both. A distal end portion of the axilla strap (4, 8) is coupled to the buckle (20) by drawing the distal end portion up through both rings (14, 15), over the second ring (15), and back down through the first ring (14). This allows for a user to pull on a distal end portion of an axilla strap (4, 8) to apply the brace, tighten or adjust the brace accordingly. This will also allow a user (7) to remove the brace by loosening a distal end portion of an axilla strap (4, 8) from around the second ring (15). It is recognized that adjustable fasteners (5) other than a buckle (20) can be utilized in the invention, such as VELCRO® hook and loop fasteners, D-rings, strap clips as utilized on back-packs, clamps or ties.

Figure 6:
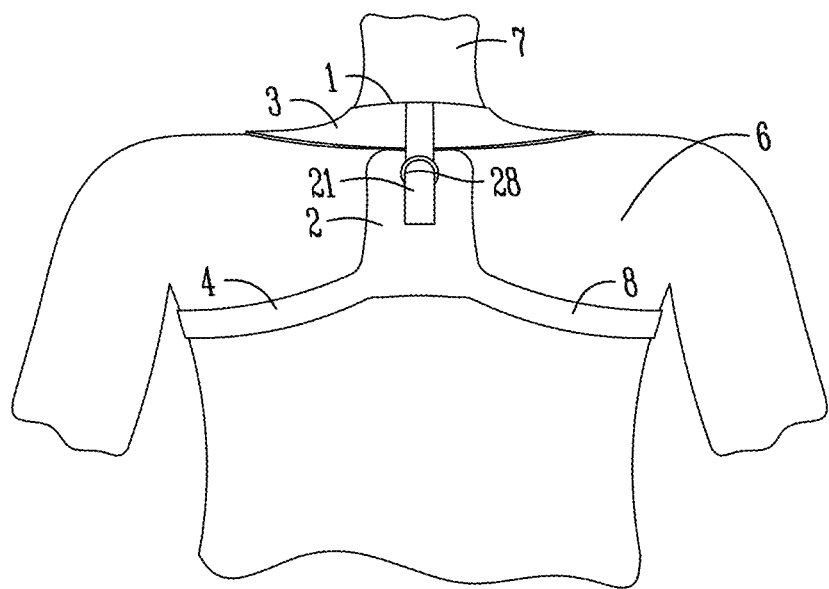

In the preferred embodiment of the invention, the clavicle brace support body (2) and the shoulder strap (3) and the first (4) and second (8) axilla straps are separate pieces and the shoulder strap (3) and the first (4) and second (8) axilla straps are connected to the clavicle brace support body (2) by adjustable fasteners (5). In another embodiment of the invention, the shoulder strap (3) is attached to the clavicle brace support body (2) by a D-ring (28) and the axilla straps (4, 8) are of a one-piece, integral construction with the body (2). See FIG. 6.

In the preferred embodiment of the invention the orthopedic clavicle brace (1) includes padded members (16) for providing cushion between the body surface of the user (7) and the shoulder strap (3) and the first (4) and second (8) axilla straps. The padded members (16) include a soft, absorbent and porous surface for contacting the user's body and absorbing sweat, providing cushion, and preventing the straps from biting into the user's shoulders and axillae. The padded members (16) can either be permanently joined to the straps or detachedly joined, such as through VELCRO® hook and loop fasteners or a sleeve-like portion for slideably fitting around said straps. Moreover, the padded members (16) can be constructed of foam, rubber, cotton, synthetic fabric, or other useful material known in the art for providing cushion, absorption and support.

The straps (3, 4, 8, 24, 25, 26) of the present invention can be flexible or elastic and preferably of ribbed type construction so as to permit expansion and contraction of the chest of the user (7) during breathing with the brace (1). Adjustable fasteners (5) permit length adjustment to accommodate persons having chests of varying sizes. In another embodiment, the straps (3, 4, 8, 24, 25, 26) are made of material which essentially does not stretch such as tension-resistant and non-stretch fabric. This achieves high therapeutic reliability, making readjustments almost unnecessary while providing stability and an ideal fit.

The user (7) self-applies the orthopedic clavicle brace (1) of the present invention by positioning the clavicle brace support body (2) substantially over his/her upper back (6) using the second (22) and third (23) end portions of the shoulder strap (3). The user then extends the second end portion (22) of the shoulder strap (3) over his/her first shoulder and attaches it by an adjustable fastener (5) thereon to the distal end portion of the first axilla strap (4) extending under the first axilla of the user (7). The user next extends the third end portion (23) of the shoulder strap (3) over his/her second shoulder and attaches it by an adjustable fastener (5) thereon to the distal end portion of the second axilla strap (8) extending under the second axilla of the user (7). The location of the adjustable fastener (5) for attaching the second end portion (22) of the shoulder strap (3) to the distal end portion of the first axilla strap (4), and the location of the adjustable fastener (5) for attaching the third end portion (23) of the shoulder strap (3) to the distal end portion of the second axilla strap (8) is towards the front (17) of the user (7). The front (17) of the user (7) is defined as the chest or thorax of the user, and can include the axilla and shoulder region of the user adjacent the chest or thorax. This location towards the front (17) of the user (7) allows the user (7) to reach up with his/her hand and grasp the adjustable fastener (5) to attach the second and third end portions (22, 23) of the shoulder strap (3) to their respective axilla straps (4, 8) to self-apply the orthopedic clavicle brace (1) of the present invention.

The user (7) self-adjusts the orthopedic clavicle brace (1) of the present invention before applying the brace and after applying the brace. The user (7) may self-adjust the orthopedic clavicle brace (1) before applying the brace by shortening or lengthening the shoulder strap (3) connected to the clavicle brace support body (2) through the adjustable fastener (5). The user (7) may self-adjust the orthopedic clavicle brace (1) after applying the brace by reaching up with his/her hands and pulling on or loosening a distal end portion of an axilla strap (4, 8) connected to the shoulder strap (3) through an adjustable fastener (5) located towards the front (17) of the user (7).

The user self-removes the orthopedic clavicle brace (1) of the present invention by reaching up with his/her hands and loosening or detaching a distal end portion of an axilla strap (4, 8) from the shoulder strap (3) through the adjustable fastener (5) located towards the front (17) of the user (7). Because of the location of the distal end portions of the axilla straps (4, 8) being towards the front (17) of the user (7), the user (7) can easily view, grasp, and adjust the straps (4, 8) without the need of help from another person.

The orthopedic clavicle brace (1) of the present invention and method for use is universally applicable to users regardless of body size or shape, simple to self-adjust properly, easy to apply or remove without needing a second person, while providing maximum support and protection to an injured clavicle. Moreover, the user can self-provide the orthopedic clavicle brace through purchase, rent, or by request of a physician or rehabilitation specialist. Although the invention has been described and illustrated with respect to preferred embodiments thereof, it is not to be so limited since changes and modifications may be made therein which are within the full intended scope of the invention.

What is claimed is:

1. An orthopedic clavicle brace for giving support to a user's shoulders to prevent or treat damage to a clavicle, said brace comprising:
   a. a clavicle brace support body configured to position substantially over an upper back of a user;
   b. a T-shaped shoulder strap having two elongated straps with three ends, the two elongated straps comprising a support connection strap and an over the shoulder strap, the support connection strap extending downwardly from a central portion of the over the shoulder strap and having a first end opposite from the over the shoulder strap along a sagittal plane of user's body, the over the shoulder strap having a second end portion and a third end portion opposite from the second end portion, wherein the T-shaped shoulder strap is attached to an upper portion of said clavicle brace support body by the first end portion of the support connection strap, such that the second end portion of the over the shoulder strap is positioned for extending over a first shoulder of the user, and the third end portion of the over the shoulder strap is for extending over a second shoulder of the user;
   c. a first axilla strap attached to a lower portion of said clavicle brace support body, said first axilla strap having a distal end portion for extending under a first axilla of the user;
   d. a second axilla strap attached to the lower portion of said clavicle brace support body adjacent said first axilla strap, said second axilla strap having a distal end portion for extending under a second axilla of the user;
   e. wherein the second end portion of the over the shoulder strap is attached to the distal end portion of the first axilla strap at a first location towards a front of the user, further wherein the first location is configured to allow for personal adjustment of the straps, application, and removal of the orthopedic clavicle brace by the user without a second party; and
   f. wherein the third end portion of the over the shoulder strap is attached to the distal end portion of the second axilla strap at a second location towards the front of the user, further wherein the second location is configured to allow for personal adjustment of the straps, application, and removal of the clavicle brace by the user without a second party.

2. The orthopedic clavicle brace of claim 1, wherein the second end portion of the shoulder strap is attached to the distal end portion of the first axilla strap at the first location towards the front of the user by a first adjustable fastener.

3. The orthopedic clavicle brace of claim 2, wherein the third end portion of the shoulder strap is attached to the distal end portion of the second axilla strap at the second location towards the front of the user by a second adjustable fastener.

4. The orthopedic clavicle brace of claim 3, wherein said shoulder strap is attached to the clavicle brace support body by a D-ring and the first and second axilla straps are of a one-piece, integral construction with the clavicle brace support body.

5. The orthopedic clavicle brace of claim 3, wherein the shoulder strap and the first and second axilla straps are attached to the clavicle brace support body by adjustable fasteners.

6. The orthopedic clavicle brace of claim 5, wherein the clavicle brace support body is triangular in shape.

7. The orthopedic clavicle brace of claim 1, further comprising padded members on said shoulder strap configured to contact a body surface of the user.

8. The orthopedic clavicle brace of claim 7, wherein the padded members are detachably joined to said shoulder strap.

9. The orthopedic clavicle brace of claim 7, wherein the padded members are permanently joined to said shoulder strap.

10. The orthopedic clavicle brace of claim 7, wherein the padded members are selected from the group consisting of foam, rubber, cotton, or synthetic fabric.

11. The orthopedic clavicle brace of claim 7, wherein the shoulder strap and said first and second axilla straps are made of material which is inelastic.

12. The orthopedic clavicle brace of claim 7, wherein the shoulder strap and said first and second axilla straps are made of elastic material.

13. An orthopedic clavicle brace for giving support to a user's shoulders to prevent or treat damage to a clavicle, said brace comprising:
   a. a clavicle brace support body configured to position substantially over an upper back of a user;
   b. a first shoulder strap attached to an upper portion of said clavicle brace support body, said first shoulder strap having a distal end portion for extending over a first shoulder of the user;
   c. a second shoulder strap attached to the upper portion of said clavicle brace support body adjacent said first shoulder strap, said second shoulder strap having a distal end portion for extending over a second shoulder of the user;
   d. a T-shaped axilla strap with three ends, the T-shaped axilla strap formed from a support body connector strap extending upwardly from an elongated axilla strap, the support body connector strap having a first end portion opposite from the elongated axilla strap, the elongated axilla strap having a second end portion and a third end portion opposite from the second end portion, the T-shaped axilla strap attached to a lower portion of said clavicle brace support body along a sagittal plane of user's body by the first end portion of the support body connector strap, the second end portion of the elongated axilla strap for extending under a first axilla of the user, and the third end portion of the elongated axilla strap for extending under a second axilla of the user;
   e. wherein the distal end portion of the first shoulder strap is attached to the second end portion of the axilla strap at a first location towards a front of the user, further wherein the first location is configured to allow for personal adjustment of the straps, application, and removal of the orthopedic clavicle brace by the user without a second party; and f. wherein the distal end portion of the second shoulder strap is attached to the third end portion of the axilla strap at a second location towards the front of the user, further wherein the second location is configured to allow for personal adjustment of the straps, application, and removal of the clavicle brace by the user without a second party.

14. The orthopedic clavicle brace of claim 13, wherein the distal end portion of the first shoulder strap is attached to the second end portion of the axilla strap at the first location towards the front of the user by a first adjustable fastener.

15. The orthopedic clavicle brace of claim 14, wherein the distal end portion of the second shoulder strap is attached to the third end portion of the axilla strap at the second location towards the front of the user by a second adjustable fastener.

16. The orthopedic clavicle brace of claim 15, wherein the first and second shoulder straps and the axilla strap are attached to the clavicle brace support body by adjustable fasteners.

17. The orthopedic clavicle brace of claim 16, further comprising padded members on said first and second shoulder straps configured to contact a body surface of the user.

* * * * *